US008172753B2

(12) United States Patent
Halmann

(10) Patent No.: US 8,172,753 B2
(45) Date of Patent: May 8, 2012

(54) SYSTEMS AND METHODS FOR VISUALIZATION OF AN ULTRASOUND PROBE RELATIVE TO AN OBJECT

(75) Inventor: Menachem Halmann, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 799 days.

(21) Appl. No.: 12/172,119

(22) Filed: Jul. 11, 2008

(65) Prior Publication Data

US 2010/0010348 A1    Jan. 14, 2010

(51) Int. Cl.
    *A61B 8/00* (2006.01)
(52) U.S. Cl. .......................................... 600/443; 128/916
(58) Field of Classification Search .......... 600/443–449; 128/916
    See application file for complete search history.

(56) References Cited

U.S. PATENT DOCUMENTS

| 5,425,370 | A  | * | 6/1995 | Vilkomerson | 600/463 |
| 6,193,657 | B1 |   | 2/2001 | Drapkin | |
| 6,216,029 | B1 | * | 4/2001 | Paltieli | 600/427 |
| 6,245,017 | B1 | * | 6/2001 | Hashimoto et al. | 600/447 |
| 6,423,002 | B1 | * | 7/2002 | Hossack | 600/439 |
| 6,544,178 | B1 | * | 4/2003 | Grenon et al. | 600/443 |
| 6,733,458 | B1 |   | 5/2004 | Steins et al. | |
| 6,761,689 | B2 | * | 7/2004 | Salgo et al. | 600/447 |
| 6,991,605 | B2 | * | 1/2006 | Lim | 600/443 |
| 7,074,185 | B2 | * | 7/2006 | Takeuchi | 600/437 |
| 7,510,536 | B2 | * | 3/2009 | Foley et al. | 601/2 |
| 7,691,062 | B2 | * | 4/2010 | Kozak et al. | 600/443 |
| 7,806,824 | B2 | * | 10/2010 | Ohtake | 600/443 |
| 2005/0090742 | A1 | * | 4/2005 | Mine et al. | 600/443 |
| 2007/0287915 | A1 | * | 12/2007 | Akaki et al. | 600/443 |
| 2009/0209859 | A1 | * | 8/2009 | Tsujita et al. | 600/445 |
| 2010/0222680 | A1 | * | 9/2010 | Hamada | 600/443 |
| 2011/0079083 | A1 | * | 4/2011 | Yoo et al. | 73/632 |

FOREIGN PATENT DOCUMENTS

CA    2273874 C    6/1998

OTHER PUBLICATIONS

Nobuyuki Taniguchi et al., Automatic virtual transducer locating system to assist in interpreting ultrasound imaging, Journal of Medical Ultrasonics, 1346-4523 (Print) 1613-2254 (Online), vol. 30, No. 4 / Dec. 2003, pp. 211-216, abstract downloaded from http://www.springerlink.com/content/d5874jun7v3276r3/?print=true, May 27, 2008.

* cited by examiner

*Primary Examiner* — Francis Jaworski

(74) *Attorney, Agent, or Firm* — The Small Patent Law Group; Dean D. Small

(57) ABSTRACT

Systems and methods for visualization of an ultrasound probe relative to an object are provided. The system includes an ultrasound probe configured to acquire ultrasound data. The system further includes a display configured to display an ultrasound image based on the ultrasound data and a graphical representation of the ultrasound probe in combination with the ultrasound image.

20 Claims, 11 Drawing Sheets

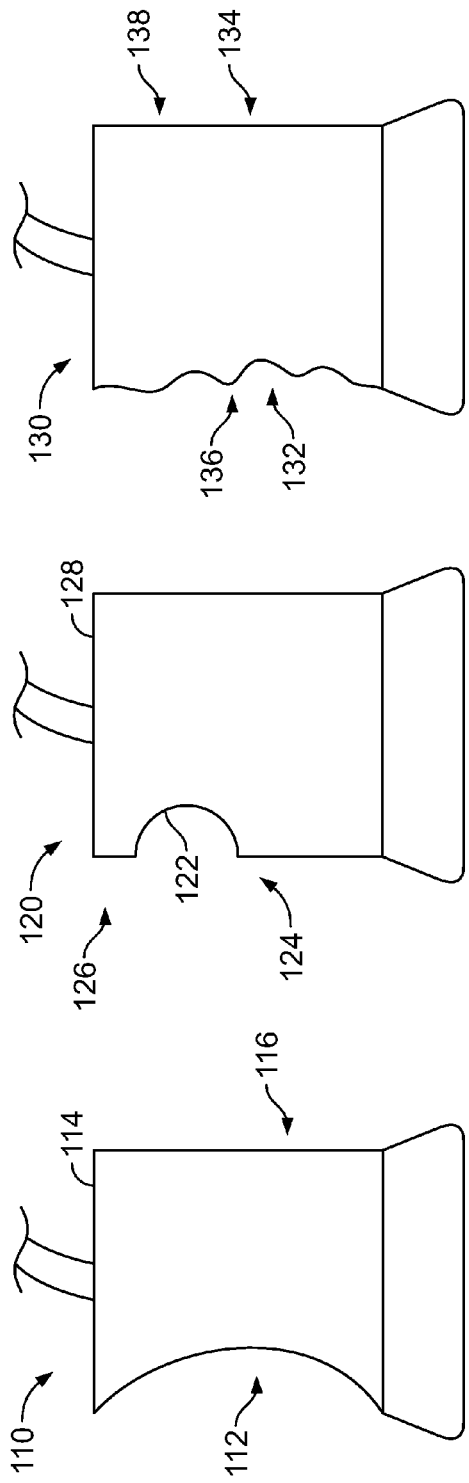

SYSTEMS AND METHODS FOR VISUALIZATION OF AN ULTRASOUND PROBE RELATIVE TO AN OBJECT

BACKGROUND OF THE INVENTION

Various embodiments of this invention relate generally to diagnostic imaging systems, and more particularly, to systems and methods that provide visualization of the relationships between three-dimensional (3D) structures inside and outside of an object of interest.

Proper orientation of an ultrasound probe to obtain desired or required images is sometimes difficult, particularly for the novice user. For example, new users to ultrasound can become perplexed by ultrasound orientation schemes. In particular, users may not fully understand or be able to readily identify which directions represent left and right or forward and backwards with respect to the ultrasound probe and the object being imaged. Moreover, even an experienced ultrasound probe user may have a misconception of the direction in which he or she thinks a probe is moving in relation to the direction the image is thought to be moving.

Understanding the relationships between internal and external 3D structures, for example, inside and outside of a patient, is not entirely trivial. In conventional ultrasound imaging systems the only indication of orientation on an ultrasound image is just a dot either on the left side or on the right side of the displayed image. The dot on the displayed image corresponds to a dot on the ultrasound probe that is being held by a user. Moreover, known ultrasound probes have a rather symmetrical shape, which can make it difficult to determine, aside from the very small dot on one side, the relative location of the front or back of the probe. In procedures involving needle injection or other invasive procedures, the need for sterility typically requires the user to cover the probe with a disposable plastic cover, making the dot invisible. Thus, a user may have to rely upon a rather high level of expertise to determine the orientation of the probe, for example, to distinguish the front from the back of the probe in order to acquire images at the proper orientation.

BRIEF DESCRIPTION OF THE INVENTION

In accordance with an embodiment of the invention, an ultrasound system is provided that includes an ultrasound probe configured to acquire ultrasound data. The ultrasound system further includes a display configured to display an ultrasound image based on the ultrasound data and a graphical representation of the ultrasound probe in combination with the ultrasound image.

In accordance with another embodiment of the invention, an ultrasound display is provided that includes a real-time ultrasound image of a three-dimensional volume and a graphical representation of an ultrasound probe acquiring ultrasound data to generate the real-time ultrasound image. The graphical representation shows one of a position and orientation of the ultrasound probe relative to the three-dimensional volume.

In accordance with yet another embodiment of the invention, a method of displaying ultrasound images is provided. The method includes displaying an ultrasound image on a display and displaying on the display in combination with the ultrasound image a graphical representation of an ultrasound probe acquiring the ultrasound image. The graphical representation identifies at least one of a position and orientation of the ultrasound probe relative to an object corresponding to the ultrasound image.

BRIEF DESCRIPTION OF THE DRAWINGS

FIG. 3 is an elevation view of an ultrasound probe constructed in accordance with an embodiment of the invention.

FIG. 4 is an elevation view of an ultrasound probe constructed in accordance with another embodiment of the invention.

FIG. 5 is an elevation view of an ultrasound probe constructed in accordance with another embodiment of the invention.

FIG. 6 is an elevation view of an ultrasound probe constructed in accordance with another embodiment of the invention.

FIG. 7 is an elevation view of an ultrasound probe constructed in accordance with another embodiment of the invention.

DETAILED DESCRIPTION OF THE INVENTION

Figure 1:
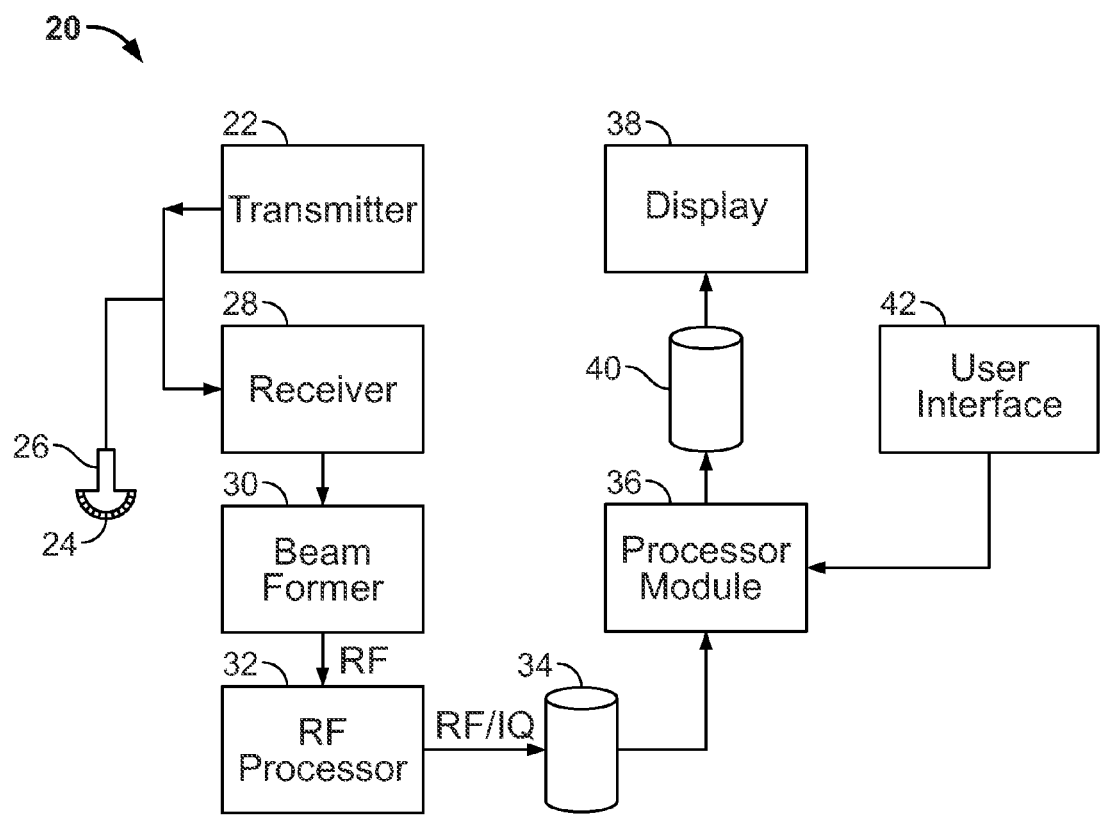
FIG. 1 is a block diagram of an ultrasound system formed in accordance with an embodiment of the invention.

The foregoing summary, as well as the following detailed description of certain embodiments of the invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although the various embodiments may be described in connection with an ultrasound system, the methods and systems described herein are not limited to ultrasound imaging. In particular, the various embodiments may be implemented in connection with different types of medical imaging, including, for example, magnetic resonance imaging (MRI) and computed-tomography (CT) imaging. Further, the various embodiments may be implemented in other non-medical imaging systems, for example, non-destructive testing systems, such as airport screening systems.

Exemplary embodiments of ultrasound systems and methods for visualizing an ultrasound probe relative to an imaged object are described in detail below. In particular, a detailed description of an exemplary ultrasound system will first be provided followed by a detailed description of various embodiments of methods and systems for displaying a representation of an ultrasound probe in combination with a displayed image, especially live or real-time three-dimensional (3D) or four-dimensional (4D) displayed images.

A technical effect of the various embodiments of the systems and methods described herein include at least one of displaying a representation of an ultrasound probe relative to a displayed imaged object to facilitate identification of an orientation or position of the ultrasound probed relative to the imaged object. An indication of a direction to move the probe also may be provided to improve the display of the imaged object.

FIG. 1 is a block diagram of an exemplary ultrasound system 20 in which the various embodiments of the invention can display a representation of an ultrasound probe as described in more detail below. The ultrasound system 20 includes a transmitter 22 that drives an array of elements 24 (e.g., piezoelectric crystals) within a transducer 26 to emit pulsed ultrasonic signals into a body or volume. A variety of geometries may be used and the transducer 26 may be provided as part of, for example, different types of ultrasound probes as described in more detail below. The ultrasonic signals are back-scattered from structures in the body, for example, blood cells, muscular tissue, veins or objects within the body (e.g., a catheter or needle) to produce echoes that return to the elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis and analysis. The display 38 may automatically display, for example, a 3D or 4D ultrasound data set stored in the memory 34 or 40 or currently being acquired, which data set is also displayed with a representation of a probe (e.g., a graphical image representation of the probe acquiring the ultrasound data). One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by moving the transducer 26, such as along a linear or arcuate path, while scanning a region of interest (ROI). At each linear or arcuate position, the transducer 26 obtains scan planes that are stored in the memory 34. The transducer 26 also may be mechanically moveable within the ultrasound probe.

Figure 2:
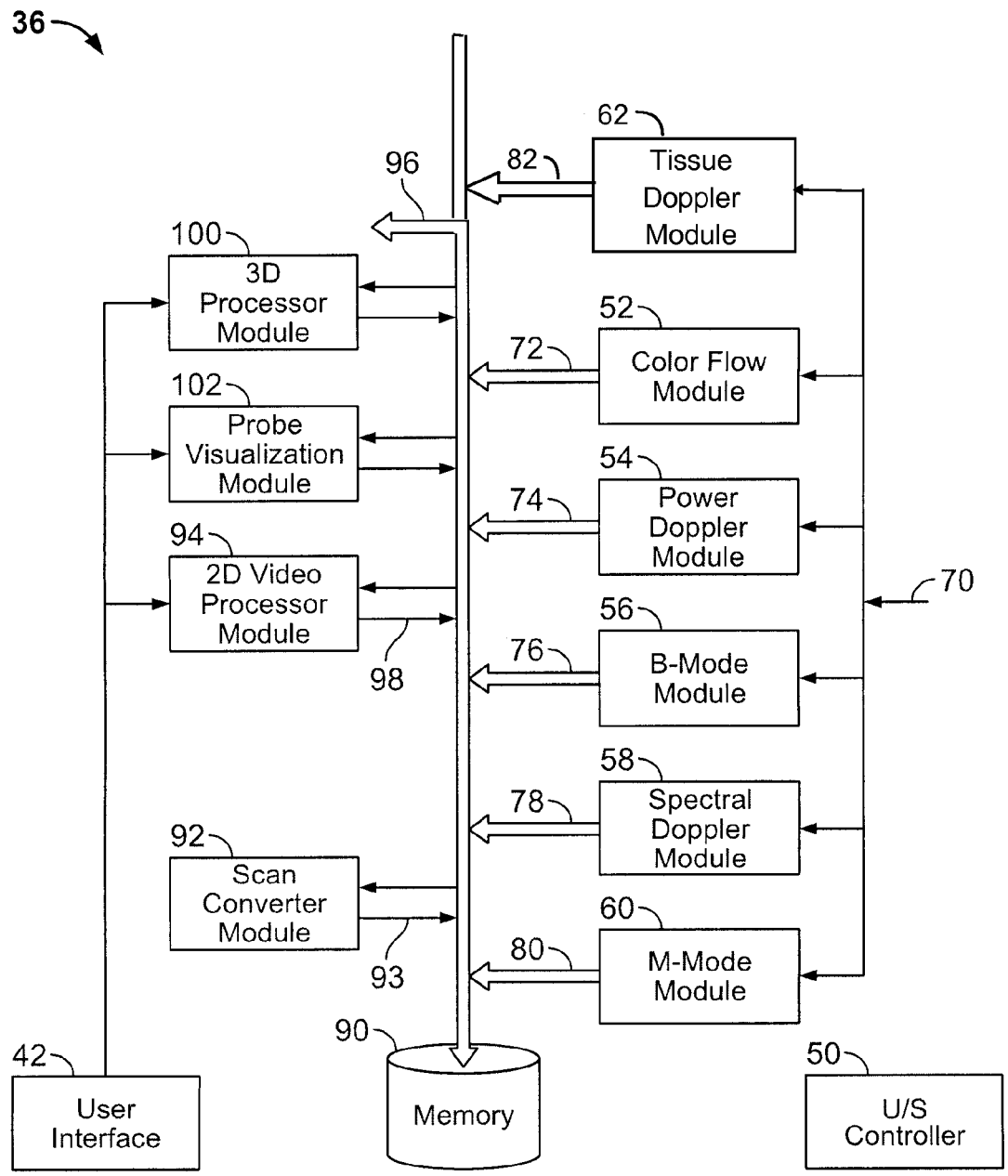
FIG. 2 is a block diagram of an ultrasound processor module of FIG. 1 formed in accordance with an embodiment of the invention.
Figure 8:
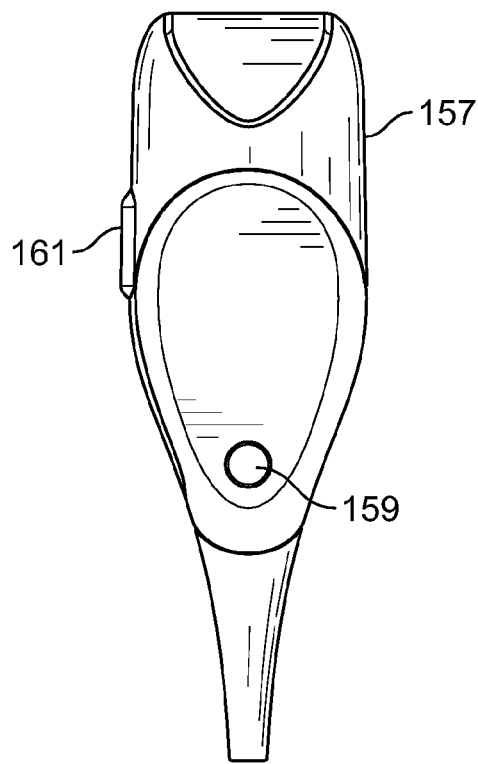
FIG. 8 is a top plan view of an ultrasound probe constructed in accordance with another embodiment of the invention.
Figure 9:
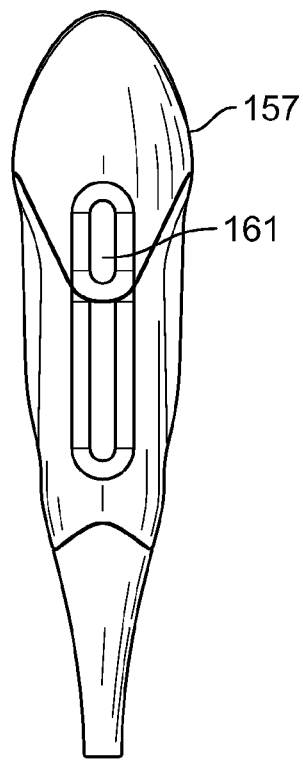
FIG. 9 is a side elevation view of the ultrasound probe of FIG. 8.
Figure 10:
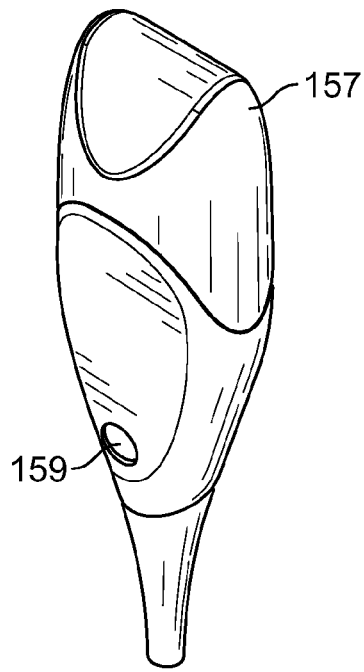
FIG. 10 is a perspective view of the ultrasound probe of FIG. 8.
Figure 11:
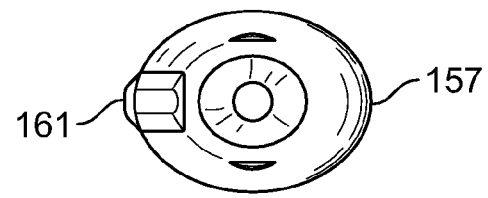
FIG. 11 is a front plan view of the ultrasound probe of FIG. 8.

FIG. 2 is an exemplary block diagram of the ultrasound processor module 36 of FIG. 1. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the-shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-62 perform mid-processor operations. The ultrasound processor module 36 may receive ultrasound data 70 in one of several forms. In the embodiment of FIG. 2, the received ultrasound data 70 constitutes IQ data pairs representing the real and imaginary components associated with each data sample. The IQ data pairs are provided to one or more sub-modules, for example, a color-flow sub-module 52, a power Doppler sub-module 54, a B-mode sub-module 56, a spectral Doppler sub-module 58 and an M-mode sub-module 60. Other sub-modules may be included, such as a Tissue Doppler (TDE) sub-module 62, among others.

Each of sub-modules 52-62 are configured to process the IQ data pairs in a corresponding manner to generate color-flow data 72, power Doppler data 74, B-mode data 76, spectral Doppler data 78, M-mode data 80, and tissue Doppler data 82, among others, all of which may be stored in a memory 90 (or memory 34 or image memory 40 shown in FIG. 1) temporarily before subsequent processing. The data 72-82 may be stored, for example, as sets of vector data values, where each set defines an individual ultrasound image frame. The vector data values are generally organized based on the polar coordinate system.

A scan converter sub-module 92 accesses and obtains from the memory 90 the vector data values associated with an image frame and converts the set of vector data values to Cartesian coordinates to generate an ultrasound image frame 93 formatted for display. The ultrasound image frames 93 generated by the scan converter sub-module 92 may be provided back to the memory 90 for subsequent processing or may be provided to the memory 34 or the image memory 40.

Once the scan converter sub-module 92 generates the ultrasound image frames 93 associated with the data, the image frames may be restored in the memory 90 or communicated over a bus 96 to a database (not shown), the memory 34, the image memory 40 and/or to other processors (not shown).

As an example, it may be desired to view different ultrasound images relating to an invasive procedure in real-time on the display 38 (shown in FIG. 1). To do so, the scan converter sub-module 92 obtains data sets for images stored in the memory 90 of that are currently being acquired. The vector data is interpolated where necessary and converted into an X,Y format for video display to produce ultrasound image frames. The scan converted ultrasound image frames are provided to a display controller (not shown) that may include a video processor that maps the video to a gray-scale mapping for video display. The gray-scale map may represent a transfer function of the raw image data to displayed gray levels. Once the video data is mapped to the gray-scale values, the display controller controls the display 38, which may include one or more monitors or windows of the display, to display the image frame. The image displayed in the display 38 is produced from an image frame of data in which each datum indicates the intensity or brightness of a respective pixel in the display.

Referring again to FIG. 2, a 2D video processor sub-module 94 may be used to combine one or more of the frames generated from the different types of ultrasound information. For example, the 2D video processor sub-module 94 may combine different image frames by mapping one type of data to a gray map and mapping the other type of data to a color map for video display. In the final displayed image, the color pixel data is superimposed on the gray scale pixel data to form a single multi-mode image frame 98 that is again re-stored in the memory 90 or communicated over the bus 96. Successive frames of images may be stored as a cine loop (4D images) in the memory 90 or memory 40 (shown in FIG. 1). The cine loop represents a first in, first out circular image buffer to capture image data that is displayed in real-time to the user. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three dimensional image representations thereof, such as through volume rendering or surface rendering algorithms as are known. The three dimensional images may be generated utilizing various imaging techniques, such as ray-casting, maximum intensity pixel projection and the like.

A probe visualization sub-module 102 is also controlled by the user interface 42 and accesses the memory 90 to obtain groups of ultrasound image frames that have been stored or that are currently being acquired and to generate three dimensional image representations thereof along with a representation (e.g., graphical image) of a probe positioned and oriented relative to the image. The three dimensional images may be generated utilizing various imaging techniques, such as ray-casting, maximum intensity pixel projection and the like. The images may be displayed using volume rendering or surface rendering algorithms as are known. The representation of the probe may be generated using a saved graphical image or drawing of the probe (e.g., computer graphic generated drawing).

Various embodiments of the invention display a representation of an ultrasound probe in combination with a displayed image of an object, for example, a live or real-time image of an object. The ultrasound probe is generally shaped asymmetrically, for example, from front to back or on different sides to facilitate displaying the relative orientation and position of the ultrasound probe. For example, as shown in FIGS. 3 through 7, the ultrasound probe may have a handle or housing of asymmetrical shape. It should be noted that although various different asymmetrical shapes of ultrasound probes are illustrated, the various embodiments are not limited to the shapes shown and any asymmetrically shaped ultrasound probe may be used. Alternatively, a symmetrically shaped ultrasound probe with an identifying mark, for example, a slot, indent, marker, etc. may be used.

More particularly, and for example as shown in FIG. 3, an ultrasound probe 110 may include one portion 112 of a handle 114 that is curved having an arcuate or concave shape and another portion 116 that is generally planar. As another example, as shown in FIG. 4, an ultrasound probe 120 may include an indented portion 122 at one area 124 of the ultrasound probe 120, for example, at a back or top portion 126 of a handle 128 of the ultrasound probe 120. The indented portion 122 may be configured to receive therein, for example, a finger (e.g., a thumb) of a user. As a further example shown in FIG. 5, an ultrasound probe 130 may include an uneven portion 132 and a generally planar portion 134 extending along different portions 136 and 138 (e.g., longitudinally), respectively, of the ultrasound probe 130. The uneven portion 132 may generally be shaped to receive the fingers of a user. As still another example shown in FIG. 6, an ultrasound probe 140 may include opposingly curved portions, for example, a concave portion 142 and a convex portion 144 extending along different areas (e.g., longitudinally) of a handle 146 of the ultrasound probe 140. As yet another example shown in FIG. 7, an ultrasound probe 150 may be tapered from a front end 152 to a back end 154 of a handle 156.

It should be noted that the shapes and sizes of the ultrasound probes shown in FIGS. 3 through 7 may be varied or modified. For example, the asymmetrical portions may be asymmetrical relative to a front and back of the probe housing or handle, different sides of the probe housing or handle, different areas of the probe housing or handle, or a combination thereof. It is contemplated that the various embodiments may be used in connection with any type of ultrasound probe wherein an orientation or position of the ultrasound probe can be identified when a representation of the ultrasound probe is displayed. As another example, a button or other control member may be positioned on one side of the probe to provide the asymmetry. For example, as shown in FIGS. 8 through 11 an ultrasound probe 157 includes a button 159 on, for example, a top surface of the ultrasound probe 157. Also, another button 161 may be included on a side of the ultrasound probe 157. Also, a grip or other raised member may be provided on a side.

Figure 12:
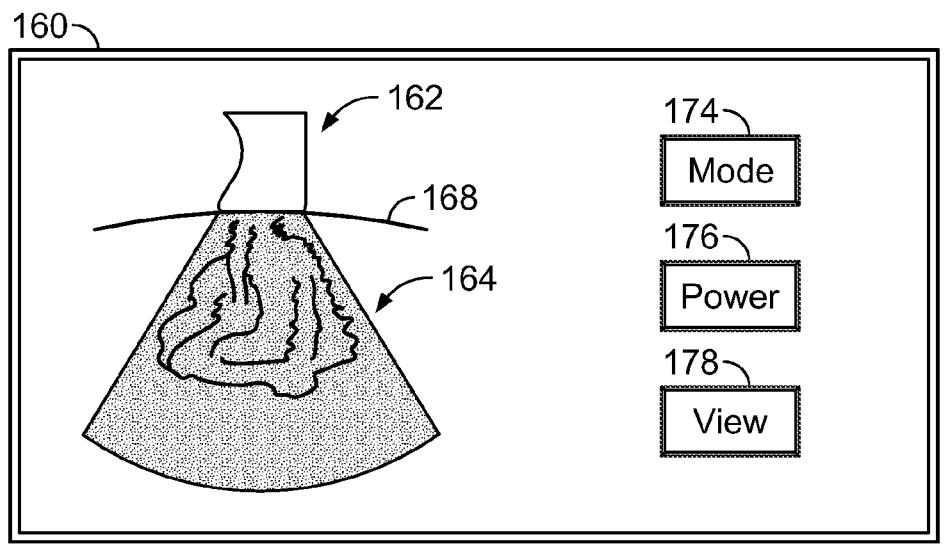
FIG. 12 is a screenshot illustrating a graphical representation of an ultrasound probe displayed in combination with an ultrasound image in accordance with an embodiment of the invention.
Figure 13:
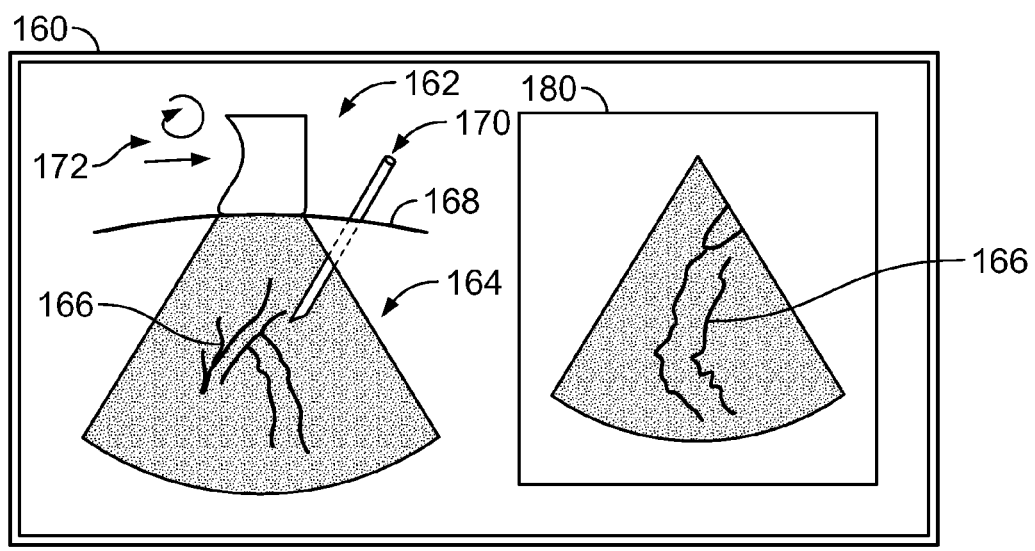
FIG. 13 is a screenshot illustrating a graphical representation of an ultrasound probe displayed in combination with an ultrasound image in accordance with another embodiment of the invention.
Figure 14:
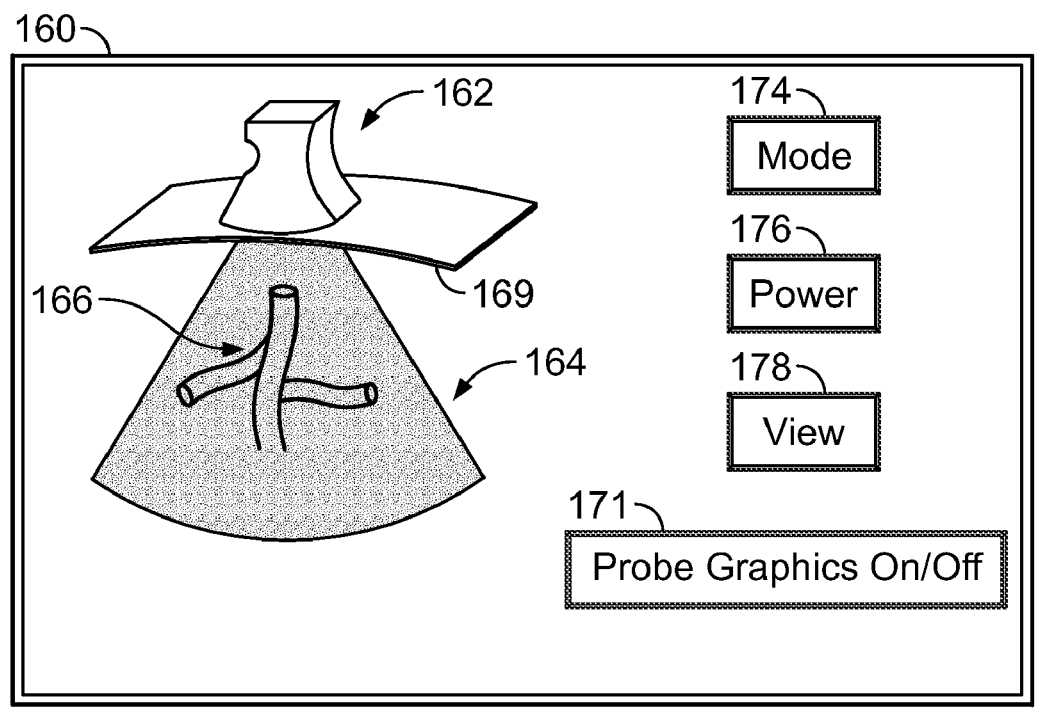
FIG. 14 is a screenshot illustrating a graphical representation of an ultrasound probe displayed in combination with an ultrasound image in accordance with another embodiment of the invention.
Figure 15:
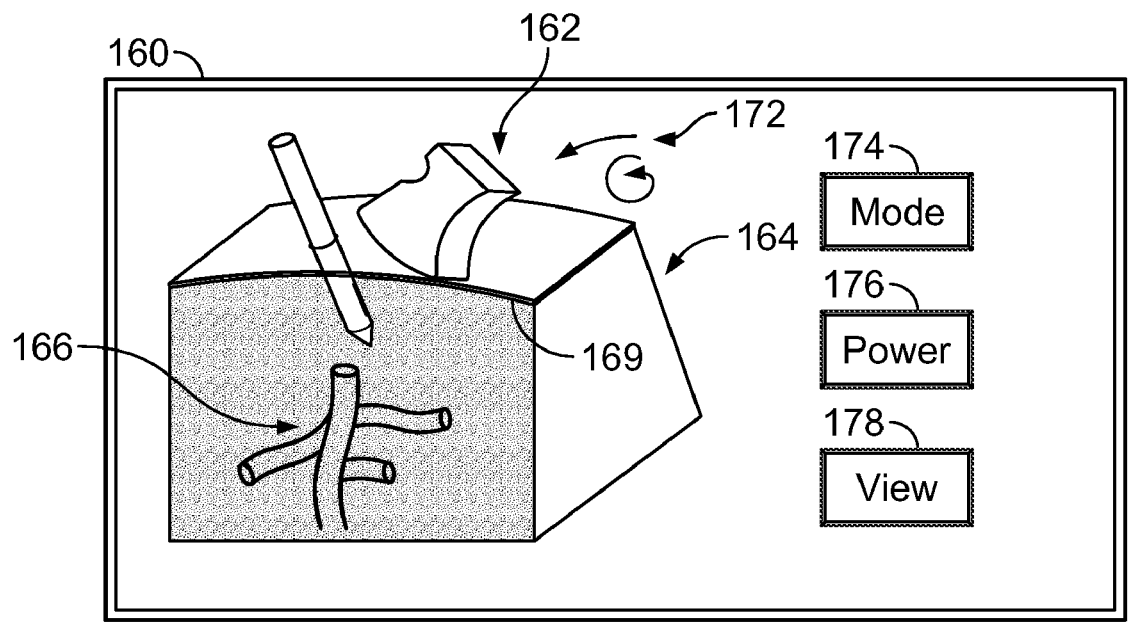
FIG. 15 is a screenshot illustrating a graphical representation of an ultrasound probe displayed in combination with an ultrasound image in accordance with another embodiment of the invention.

More particularly, and as shown in FIGS. 12 through 15, various embodiments of the invention display a representation of an ultrasound probe on the same screen as a displayed ultrasound image, which may be displayed in relative proximity to the displayed ultrasound image. For example, as shown in FIGS. 12 and 13, illustrating a screen 160, for example, the display 38 of the ultrasound system 20 of FIG. 1, a graphical representation 162 of an ultrasound probe (e.g., the ultrasound probes of FIGS. 3 through 11) is displayed in combination with an ultrasound image 164, for example, in proximity to or adjacent the ultrasound image. More particularly, the graphical representation 162 may be an image of the ultrasound probe currently being used to acquire the ultrasound image 164 displayed on the screen 160. The graphical representation 162 generally shows the shape of the housing of the ultrasound probe to allow a determination of a current orientation and/or position of the ultrasound probe relative to an object being scanned and displayed as the ultrasound image 164. The graphical representation 162 is a 2D image in the screens 160 of FIGS. 12 and 13, however, the image may be 3D as shown in FIGS. 14 and 15. It should be noted that the graphical representation 162 may be decreased in one or more dimensions (e.g., made smaller longitudinally) to take up less space on the screen 160.

The ultrasound image 164 in some embodiments is a live or real-time 3D image being (e.g., dynamic 3D rendering of an acquired volume) acquired by the ultrasound probe (which is represented on the screen by the graphical representation 162), for example, a neonatal ultrasound image or an image of a lumen 166, such as a vein. When imaging a patient, a skin line 168 is also displayed that represents and identifies the skin of the patient being imaged. The skin line 168 generally defines the border between the probe and the imaged object.

If an invasive procedure is being performed, the object being inserted within the patient is also displayed. In particular, below the skin line 168, a real-time or actual image of a portion of an invasive object 170 (e.g., needle or catheter) that is within the patient is displayed along with the imaged object, which may include the lumen 166 into which the invasive object 170 is to be inserted. Above the skin line 168, a representation of another portion of the invasive object 170 that is outside the patient is displayed, for example, by using extrapolation of the shape of the object as described in more detail below. The portions of the invasive object 170 displayed above and below the skin line 168 together may represent all or most of the invasive object 170.

Additionally or optionally, one or more indictors 172 may be displayed on the screen 160. The indicators 172 may be, for example, arrows indicating a direction or rotation to move the ultrasound probe such that the ultrasound probe is positioned or oriented differently. However, other feedback may be provided to the user regarding how to move or orient the probe (e.g., the ultrasound probes of FIGS. 3 through 11), for example, audio commands or displayed textual messages. The movement may identify, for example, an improved or optimum positioning or orientation of the probe to better visualize the imaged object. For example, when imaging a lumen 166 the best image may be acquired when the ultrasound probe is positioned above the lumen 166. In the example shown, the indicators 172 indicate that the ultrasound probe should be moved right and rotated clockwise relative to the patient. When a user moves the ultrasound probe, the graphical representation 162 is updated and changes to show the new position of the ultrasound probe relative to the imaged object displayed as the ultrasound image 164. Because of the asymmetrical shape of the housing of the ultrasound probe, the positioning and orientation (and changes thereof) of the ultrasound probe relative to the imaged object can be identified. Additionally, the indicators 172 are updated as the ultrasound probe is moved.

Additional information or selectable members may be provided on the screen 160. For example, a mode selector portion 174, power selector portion 176 and/or a view selector portion 178 may be provided to allow a user to select different scanning modes, power modes and display modes, respectively. The selector portions 174-178 may be selectable elements and that also may display information related to the selected option, level, etc. Also, and for example, a probe graphics on/off selectable member 171 may be provided to allow a user to turn on and off the graphical representation 162 such that the graphical representation 162 is displayed when in an on state and not displayed when in an off state. It should be noted that any information, whether graphical, textual or images may be displayed as is known in ultrasound systems. As another example, an enlarged ultrasound image 180 may be displayed showing a particular portion of the imaged object, for example, a portion of the lumen 166.

It should be noted that graphical representation 162 also may be a 3D image as shown in FIGS. 14 and 15. Accordingly, movement of the ultrasound probe relative to the imaged object changes the positioning and orientation of the graphical representation 162 relative to the displayed image 164, and in particular, the 3D graphical representation in three dimensions. The indicators 172 may indicate in three dimensions a movement of the ultrasound probe to, for example, improve the displayed image 164 or better orient the image for a particular scan. Also, in the embodiments of FIGS. 10 and 11 a skin plane 169 may be provided instead of a skin line 168.

It should be noted, however, that the various embodiments may be implemented in connection with either 2D or 3D, or a combination thereof. For example, if a 3D probe is used, the display may be a live or real-time 2D display. Accordingly, although the probe is capable of acquiring a volume in real-time, and does acquire live volumes, only live or real-time 2D slices may be displayed. Additionally, and for example, the slice may be an "ideal" slice based on an imaging processing algorithm that detects vessels, needles or both. If the probe is a 3D probe and a live or real-time 2D slice is being displayed, user controls, for example, through the user interface 42 (shown in FIG. 1) may be used to move and rotate the slice. The various embodiments then automatically adjust the graphical representation 162 relative to the 3D image.

It also should be noted that volumes of 3D acquisition may be stored and archived for future processing, either on the ultrasound system 20 (shown in FIG. 1) or a workstation, separate processing unit, etc. During such post-processing, the graphical representation 162 is still displayed, as well as the skin line 168 or skin plane 169 even though the imaging is not live or real-time. The graphical representation 162 is still updated, for example, the orientation and position changed based on changes to the displayed image.

Figure 16:
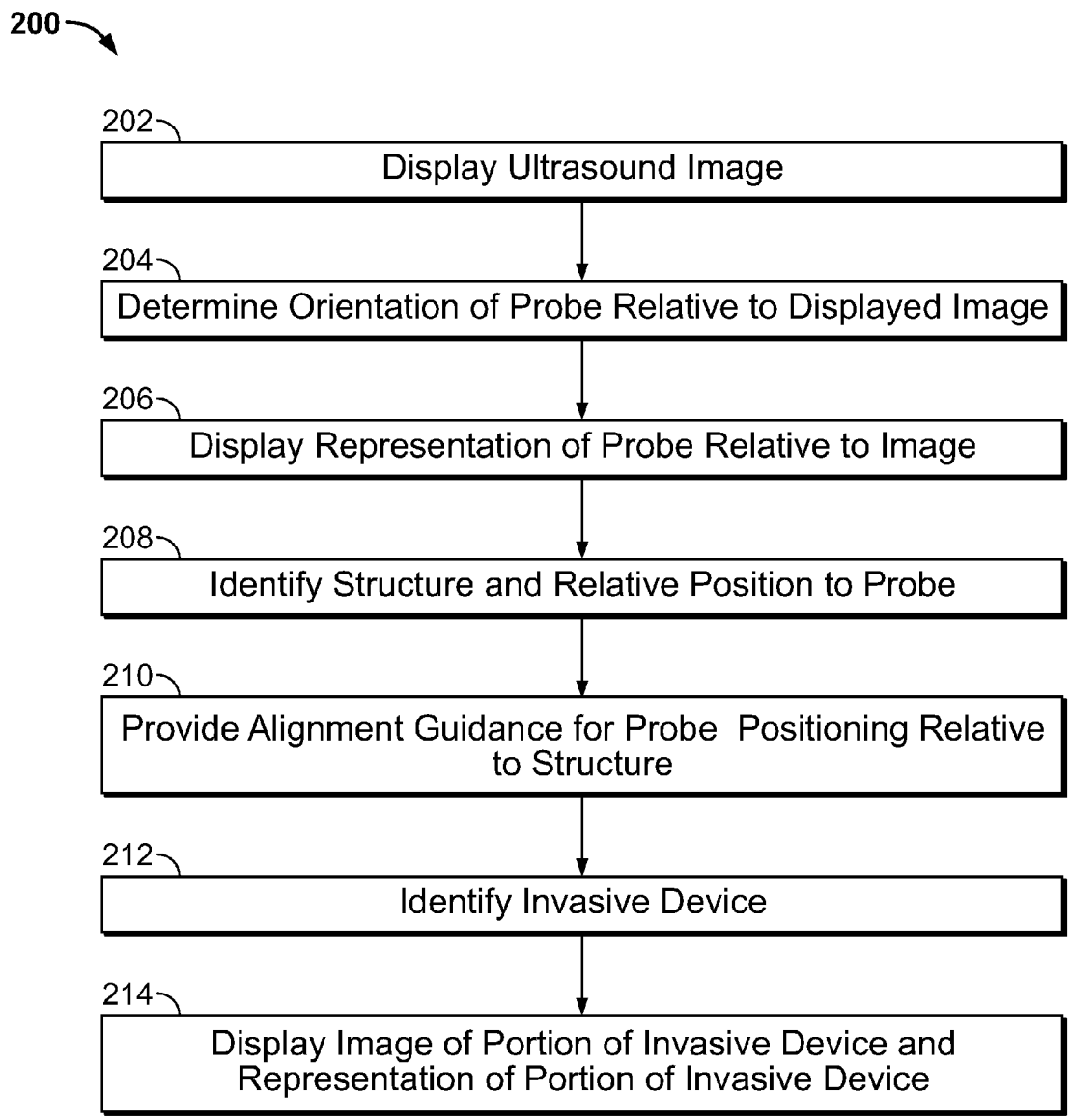
FIG. 16 is a flowchart of a method for displaying a representation of an ultrasound probe to graphically illustrate an orientation and position of the ultrasound probe relative to an imaged object in accordance with an embodiment of the invention.

Accordingly, various embodiments of the invention display a representation of an ultrasound probe to graphically illustrate an orientation and position of the ultrasound probe relative to an imaged object. In particular, a method 200 of various embodiments as shown in FIG. 16 includes displaying an ultrasound image at 202. For example, a live or real-time 3D volume that is currently or has been acquired is displayed using any known ultrasound display method. Thereafter, an orientation (and positioning) of the ultrasound probe relative to the imaged object is determined at 204 using any known process. For example, based on the current mode of scanning and the geometry of the ultrasound probe (which is known), the orientation and positioning of the ultrasound probe relative to the imaged volume may be determined. For example, the tilt, rotation and position of the ultrasound probe on the skin of a patient are determined relative to the acquired imaged volume using the known geometry and scanning parameters of the ultrasound probe. However, it should be noted that other orientation and positioning means may be used, for example, an internal or external position detection device.

Once the orientation and positioning of the ultrasound probe relative to the imaged volume is determined, a representation (e.g., a graphical representation or graphical image) of the ultrasound probe is displayed relative to an image of the acquired volume at 206, for example, above or adjacent a skin line displayed on a screen. Thereafter, at 208 a structure and relative position of the structure relative to the probe is identified. For example, using ultrasound echoes, the relative position of a lumen within a patient may be identified and displayed as part of the displayed volume. Based on the identified position (and determined coordinates within the volume) of the structure and orientation and position of the ultrasound probe, alignment guidance may be provided at 210, for example, by displaying one or more indicators. For example, the indictors may show a direction or orientation to move the probe to position the probe above the identified structure to better image the structure. As the ultrasound probe is moved the indicators are updated accordingly. Thus, when the ultrasound probe is moved to a desired or required position and/or orientation, the indicators disappear or an indicator that the desired or required position has been obtained is provided.

Thereafter, an invasive device optionally may be identified at 212, for example, when an invasive procedure is being performed. For example, using ultrasound echoes, a catheter or needle within a patient may be identified and imaged. The needle, for example, has an acoustic impact on the image, in that the needle looks different than other elements and structures in the image. The position and orientation of the catheter or needle is determined based on, for example, the coordinates of the catheter or needle within the imaged volume as imaged. A portion of the catheter or needle outside the imaged volume (e.g., outside the skin) may then be determined using extrapolation, for example, using the known straight shape of the catheter or needle. The invasive device is then displayed at 214. For example, an actual image of the invasive device is displayed below the skin line and a representation of the invasive device is displayed above the skin line.

Thus, the various embodiments allow a user, when the user sees the shape of ultrasound probe on a screen, to relate the shape to the shape of the ultrasound probe being used to perform the scan. Also, using a known algorithm that automatically finds, for example, a lumen or vessel of interest, if that lumen or vessel of interest is slightly off center with respect to the ultrasound probe, with a 3D probe the lumen or vessel (e.g., the artery or the vein), can be imaged even if the lumen or vessel is not directly beneath the center of the ultrasound probe. However, for optimal guidance in an invasive procedure (e.g., needle guidance or catheter guidance) the ultrasound probe should be aligned on top of the lumen or vessel. Accordingly, indicators, such as arrows adjacent the representation (e.g., rendering) of the ultrasound probe can inform the user that he or she needs to move the ultrasound probe forward, backwards, left, or right, or rotate the probe clockwise or counterclockwise. A user can also correlate, for example, a needle the user is holding in his or her other hand to graphical and ultrasound representations outside and inside the skin, respectively as described herein.

It should be noted that with respect to invasive procedures, the various embodiments may be used with free hand invasive device (e.g., needle) guidance or when using a guidance bracket. A guidance bracket holds, for example, the needle so that the needle can only move in a certain trajectory. When performing a guided procedure with this guided bracket, the above skin line visualization can be used to position and orient the ultrasound probe.

Figure 17:
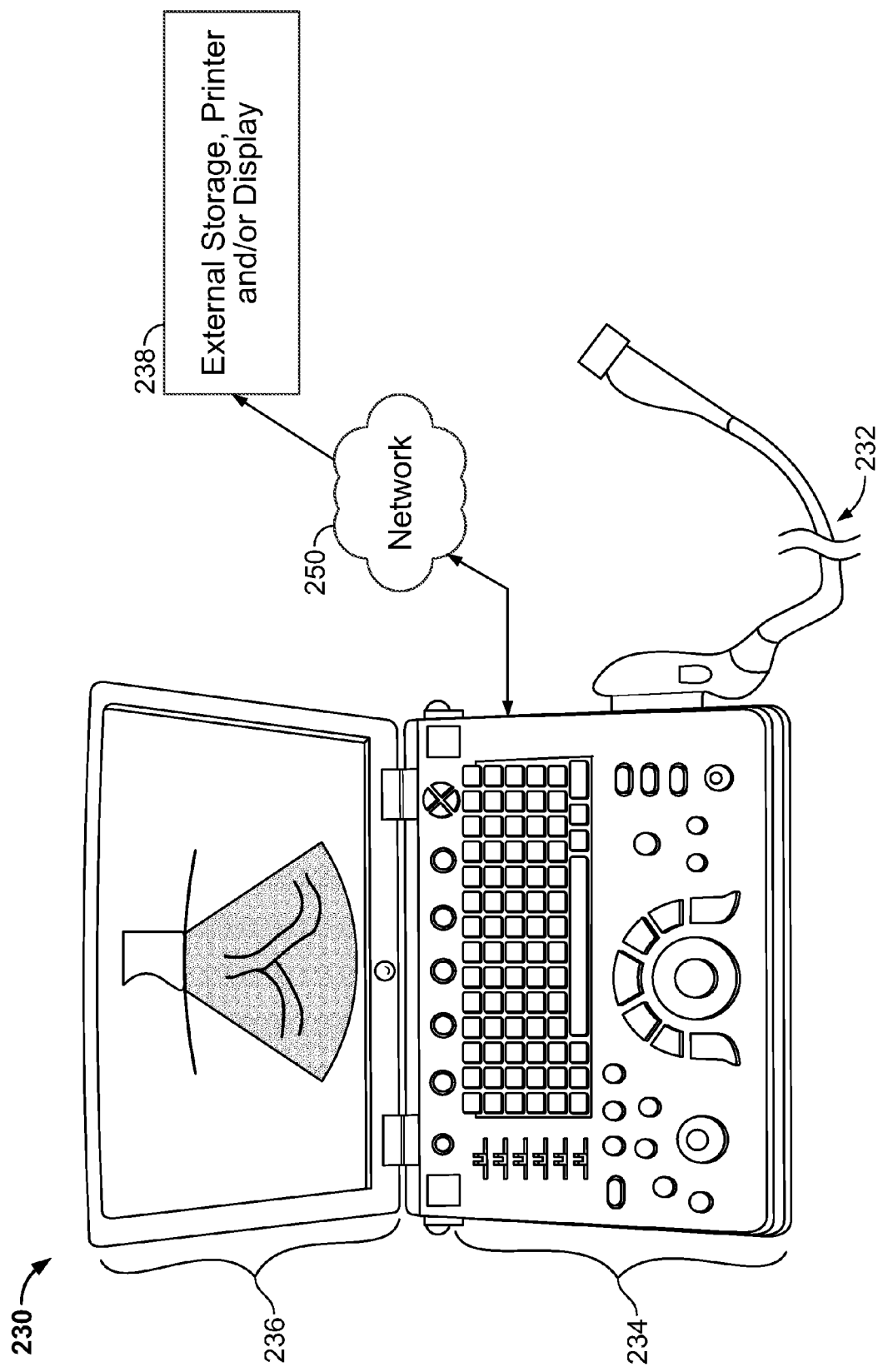
FIG. 17 illustrates a miniaturized ultrasound imaging system that may be configured to display a graphical representation of an ultrasound probe in accordance with various embodiments of the invention.

It also should be noted that the various embodiments may be implemented in connection with different types and kinds of ultrasound systems. For example, as shown in FIG. 17, a 3D-capable miniaturized ultrasound imaging system 230 having a probe 232 may be configured to display the graphical representation of the probe 232. For example, the probe 232 may have a 2D array of transducer elements 24 as discussed previously with respect to the transducer 26 of FIG. 1. A user interface 234 (that may also include an integrated display 236) is provided to receive commands from an operator. As used herein, "miniaturized" means that the ultrasound system 230 is a handheld or hand-carried device or is configured to be carried in a person's hand, pocket, briefcase-sized case, or backpack. For example, the ultrasound system 230 may be a hand-carried device having a size of a typical laptop computer, for instance, having dimensions of approximately 2.5 inches in depth, approximately 14 inches in width, and approximately 12 inches in height. The ultrasound system 230 may weigh about ten pounds, and thus is easily portable by the operator. The integrated display 236 (e.g., an internal display) is also provided and is configured to display a medical image.

The ultrasonic data may be sent to an external device 238 via a wired or wireless network 250 (or direct connection, for example, via a serial or parallel cable or USB port). In some embodiments, external device 238 may be a computer or a workstation having a display. Alternatively, external device 238 may be a separate external display or a printer capable of receiving image data from the hand carried ultrasound system 230 and of displaying or printing images that may have greater resolution than the integrated display 236.

Figure 18:
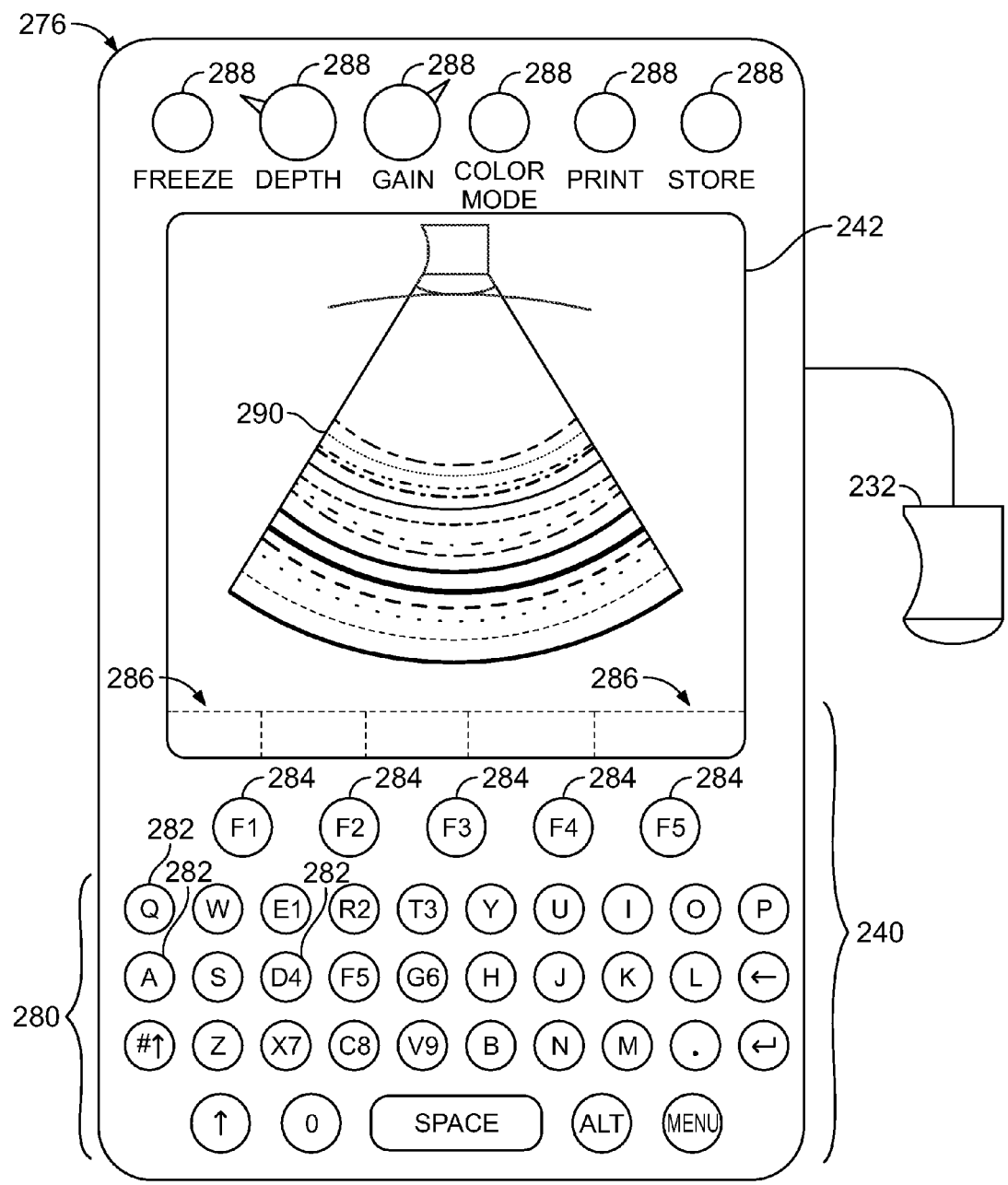
FIG. 18 illustrates a hand carried or pocket-sized ultrasound imaging system that may be configured to display a graphical representation of an ultrasound probe in accordance with various embodiments of the invention.

As another example shown in FIG. 18, a hand carried or pocket-sized ultrasound imaging system 276 may be provided and configured to display the graphical representation of the probe 232. In the system 276, display 242 and user interface 240 form a single unit. By way of example, the pocket-sized ultrasound imaging system 276 may be a pocket-sized or hand-sized ultrasound system approximately 2 inches wide, approximately 4 inches in length, and approximately 0.5 inches in depth and weighs less than 3 ounces. The display 242 may be, for example, a 320×320 pixel color LCD display (on which a medical image 290 may be displayed in combination with a graphical representation of the probe 232). A typewriter-like keyboard 280 of buttons 282 may optionally be included in the user interface 240. It should be noted that the various embodiments may be implemented in connection with a pocket-sized ultrasound system 276 having different dimensions, weights, and power consumption.

Multi-function controls 284 may each be assigned functions in accordance with the mode of system operation. Therefore, each of the multi-function controls 284 may be configured to provide a plurality of different actions. Label display areas 286 associated with the multi-function controls 284 may be included as necessary on the display 242. The system 276 may also have additional keys and/or controls 288 for special purpose functions, which may include, but are not limited to "freeze," "depth control," "gain control," "color-mode," "print," and "store."

Figure 19:
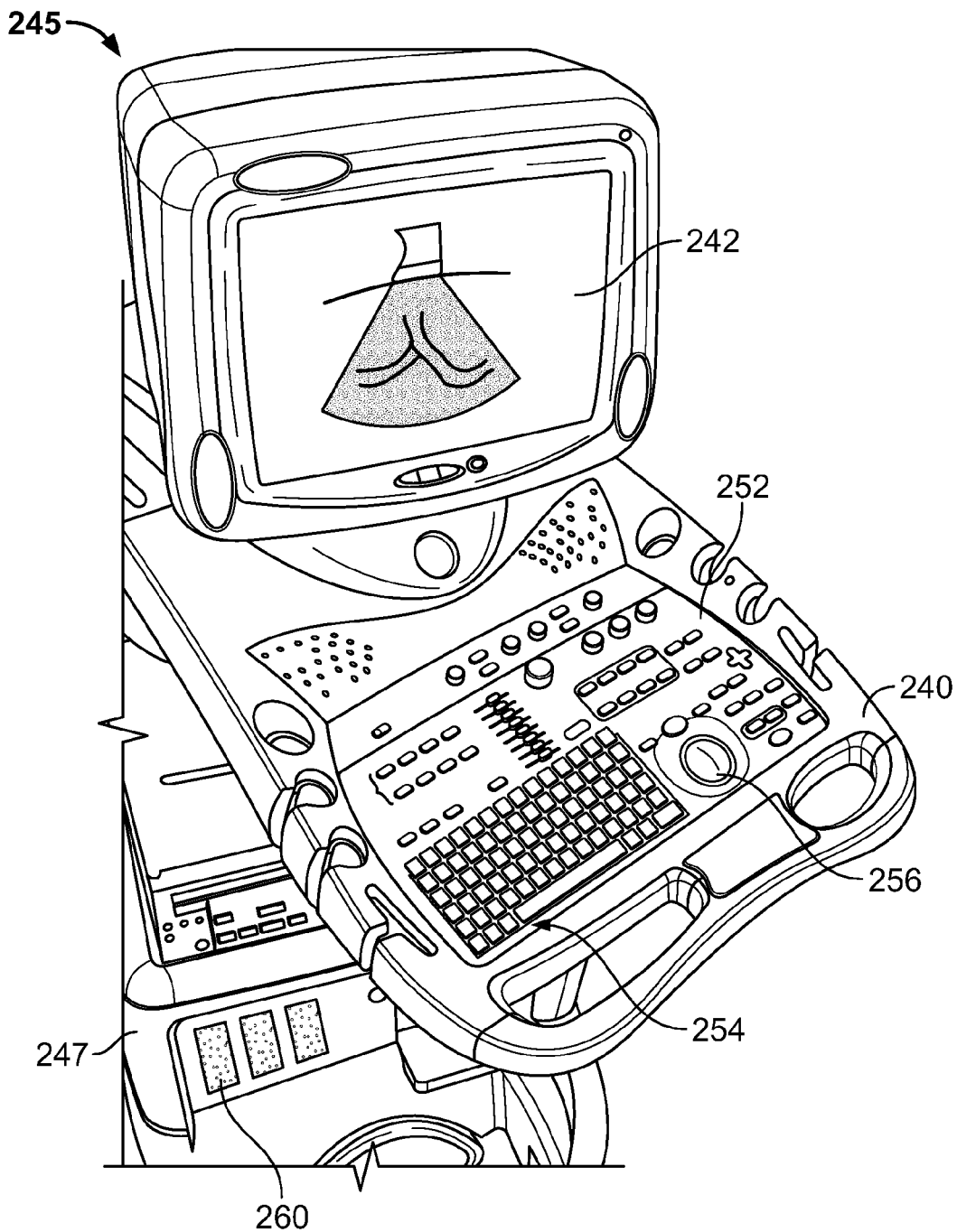
FIG. 19 illustrates a console-based ultrasound imaging system provided on a movable base that may be configured to display a graphical representation of an ultrasound probe in accordance with various embodiments of the invention.

As another example shown in FIG. 19, a console-based ultrasound imaging system 245 may be provided on a movable base 247 that may be configured to display the graphical representation of the probe 232 (shown in FIGS. 18 and 19). The portable ultrasound imaging system 245 may also be referred to as a cart-based system. A display 242 and user interface 240 are provided and it should be understood that the display 242 may be separate or separable from the user interface 240. The user interface 240 may optionally be a touchscreen, allowing the operator to select options by touching displayed graphics, icons, and the like.

The user interface 240 also includes control buttons 252 that may be used to control the portable ultrasound imaging system 245 as desired or needed, and/or as typically provided. The user interface 240 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 254 and track ball 256 may be provided. The system 245 has at least one probe port 160 for accepting probes.

Figure 20:
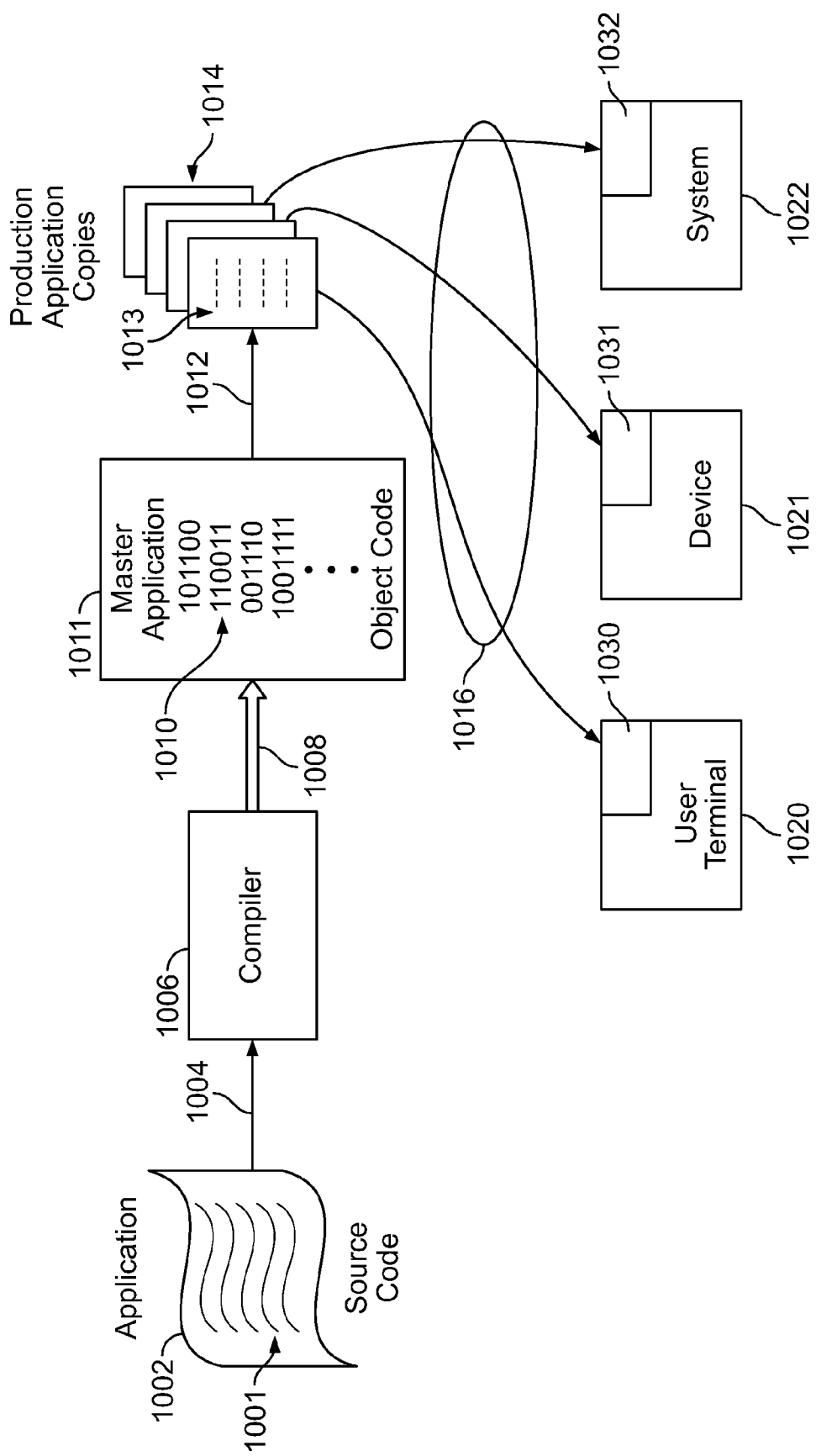
FIG. 20 is a block diagram of exemplary manners in which embodiments of the invention may be stored, distributed and installed on computer readable medium.

FIG. 20 is a block diagram of exemplary manners in which embodiments of the present invention may be stored, distributed and installed on computer readable medium. In FIG. 20, the "application" represents one or more of the methods and process operations discussed above. For example, the application may represent the process carried out in connection with FIG. 16 as discussed above.

As shown in FIG. 20, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous times, as denoted by path 1012, to produce production application copies 1013 that are saved on separate production computer readable medium 1014. The production computer readable medium 1014 is then conveyed, as denoted by path 1016, to various systems, devices, terminals and the like. In the example of FIG. 20, a user terminal 1020, a device 1021 and a system 1022 are shown as examples of hardware components, on which the production computer readable medium 1014 are installed as applications (as denoted by 1030-1032).

The source code may be written as scripts, or in any high-level or low-level language. Examples of the source, master, and production computer readable medium 1002, 1011 and 1014 include, but are not limited to, CDROM, RAM, ROM, Flash memory, RAID drives, memory on a computer system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011 or 1014 between two geographic locations. The paths 1004, 1008, 1012 and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, inter-continental and the like.

The operations noted in FIG. 20 may be performed in a widely distributed manner world-wide with only a portion thereof being performed in the United States. For example, the application source code 1001 may be written in the United States and saved on a source computer readable medium 1002 in the United States, but transported to another country (corresponding to path 1004) before compiling, copying and installation. Alternatively, the application source code 1001 may be written in or outside of the United States, compiled at a compiler 1006 located in the United States and saved on a master computer readable medium 1011 in the United States, but the object code 1010 transported to another country (corresponding to path 1012) before copying and installation. Alternatively, the application source code 1001 and object code 1010 may be produced in or outside of the United States, but production application copies 1013 produced in or conveyed to the United States (e.g. as part of a staging operation) before the production application copies 1013 are installed on user terminals 1020, devices 1021, and/or systems 1022 located in or outside the United States as applications 1030-1032.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound system comprising:
an ultrasound probe configured to acquire ultrasound data of an object; a processor module configured to process the acquired ultrasound data for display, and
a display responsive to the processor module to display a three-dimensional (3D) ultrasound image volume based on the ultrasound data and a 3D graphical representation of the ultrasound probe in combination with the ultrasound image showing a position of the 3D graphical representation of the ultrasound probe at the displayed 3D ultrasound image volume corresponding to a 3D position of the ultrasound probe relative to the 3-D ultrasound image volume of the imaged object.

2. An ultrasound image in accordance with claim 1 wherein the ultrasound probe comprises an asymmetrically shaped housing.

3. An ultrasound image in accordance with claim 2 wherein the asymmetrically shaped housing comprises a curved region.

4. An ultrasound image in accordance with claim 2 wherein the asymmetrically shaped housing comprises an indented portion.

5. An ultrasound image in accordance with claim 2 wherein the asymmetrically shaped housing comprises an uneven portion.

6. An ultrasound image in accordance with claim 1 wherein the 3D graphical representation of the ultrasound probe comprises an image of the ultrasound probe showing one of an orientation and a position of the ultrasound probe relative to the ultrasound image.

7. An ultrasound image in accordance with claim 1 wherein the display is configured to update one of an orientation and position of the 3D graphical representation of the ultrasound probe based on a movement of the ultrasound probe.

8. An ultrasound image in accordance with claim 1 wherein the display of the 3D graphical representation of the ultrasound probe is at least on a portion of the 3D image.

9. An ultrasound image in accordance with claim 1 wherein the display is configured to display a skin line between the 3D graphical representation of the ultrasound probe and the ultrasound image.

10. An ultrasound image in accordance with claim 1 wherein the display is configured to display at least one indicator to indicate at least one of a movement direction and rotation for the ultrasound probe.

11. An ultrasound image in accordance with claim 1 further comprising an invasive device and wherein the display is configured to display the invasive device in combination with the ultrasound image.

12. An ultrasound image in accordance with claim 1 further comprising an invasive device and wherein the display is configured to display an extrapolated representation of the invasive device.

13. An ultrasound image in accordance with claim 1 wherein the 3D graphical representation of the ultrasound probe comprises a computer graphic generated drawing.

14. An ultrasound image in accordance with claim 1 wherein the 3D graphical representation of the ultrasound probe shows 3D position and orientation of the ultrasound probe relative to the object imaged by the ultrasound probe.

15. An ultrasound imaging display method comprising generating a format comprising:
 display of a three-dimensional (3D) real-time ultrasound image of a 3D volume; and
 display of a 3D graphical representation of an ultrasound probe at the real-time 3D ultrasound image, the 3D graphical representation showing one of a position or orientation of the ultrasound probe corresponding to the displayed 3D volume at a surface of the 3D volume.

16. An ultrasound imaging display format in accordance with claim 15 wherein the 3D ultrasound volume comprises a portion of a patient.

17. An ultrasound imaging display format in accordance with claim 15 further comprising a skin line identifying the skin boundary between the ultrasound probe and the 3D volume.

18. An ultrasound imaging display format in accordance with claim 15 wherein one of the position and orientation of the graphical representation of the ultrasound probe is updated based on movement of the ultrasound probe.

19. An ultrasound imaging display format in accordance with claim 15 further comprising a display of an invasive device that is updated based on movement of the invasive device.

20. A method of displaying ultrasound images, the method comprising:
 displaying a three-dimensional (3D) ultrasound image of a 3D volume on a display; and
 displaying on the display at the ultrasound image a 3D graphical representation of an ultrasound probe acquiring the ultrasound image, the 3D graphical representation identifying at least one of a position or orientation of the ultrasound probe relative to a surface of the displayed 3D volume corresponding to the displayed 3D graphical representation of the ultrasound probe.

* * * * *